United States Patent [19]

Rall et al.

[11] Patent Number: 5,529,064
[45] Date of Patent: Jun. 25, 1996

[54] SENSOR DEVICE FOR MEASURING VITAL PARAMETERS OF A FETUS DURING LABOR AND DELIVERY

[76] Inventors: Gerhard Rall, Bozzaristrasse 39f, 81545 Muenchen; Reinhold Knitza, Bergstrasse 3, 82131 Gauting, both of Germany

[21] Appl. No.: 197,528

[22] Filed: Feb. 16, 1994

[30] Foreign Application Priority Data

Feb. 16, 1993 [DE] Germany .................... 43 04 693.2

[51] Int. Cl.⁶ .............................. A61B 5/00; A61B 5/042
[52] U.S. Cl. ........................................... 128/633; 128/642
[58] Field of Search ...................... 128/633, 634, 128/642

[56] References Cited

U.S. PATENT DOCUMENTS

| | | |
|---|---|---|
| 4,281,659 | 8/1981 | Farrar et al. . |
| 4,299,232 | 11/1981 | Zilianti . |
| 4,476,871 | 10/1984 | Hon . |
| 4,658,825 | 4/1987 | Hochberg et al. . |
| 4,825,879 | 5/1989 | Tan et al. . |
| 4,936,306 | 6/1990 | Doty . |
| 4,938,218 | 7/1990 | Goodman et al. . |
| 5,099,842 | 3/1992 | Mannheimer et al. . |
| 5,109,849 | 5/1992 | Goodman et al. . |
| 5,139,033 | 8/1992 | Everett et al. . |
| 5,154,175 | 10/1992 | Gunther . |
| 5,188,108 | 2/1993 | Secker . |
| 5,217,013 | 6/1993 | Lewis et al. . |
| 5,224,478 | 7/1993 | Sakai et al. . |
| 5,246,003 | 9/1993 | DeLonzor . |
| 5,247,932 | 9/1993 | Chung et al. . |
| 5,377,673 | 1/1995 | Dell et al. .................. 128/633 |
| 5,419,322 | 5/1995 | Joseph et al. . |

FOREIGN PATENT DOCUMENTS

| | | |
|---|---|---|
| 0097454A2 | 1/1984 | European Pat. Off. . |
| 0104619 | 4/1984 | European Pat. Off. . |
| 0135840 | 4/1985 | European Pat. Off. . |
| 0442011 | 8/1991 | European Pat. Off. . |
| 0451560A2 | 10/1991 | European Pat. Off. . |
| 2619471 | 11/1977 | Germany . |
| 3810008 | 3/1988 | Germany . |
| 89/00170 | 2/1989 | WIPO . |
| 89/09016 | 10/1989 | WIPO . |
| 90/01293 | 2/1990 | WIPO . |
| 90/04352 | 5/1990 | WIPO . |

OTHER PUBLICATIONS

König, Volker, FIG. 1–copy of slide shown in Kloster Banz, 8623 Staffelstein, Sep. 27–30, 1992.

Y. Mendelson & B. Ochs, "Noninvasive Pulse Oximetry Utilizing Skin Reflectance Photoplethysmography," *IEEE Transactions on Biomedical Engineering*, vol. 35, No. 10, pp. 798–805 (Oct. 1988).

*Primary Examiner*—Lee S. Cohen
*Attorney, Agent, or Firm*—Burns, Doane, Swecker & Mathis

[57] ABSTRACT

A sensor device used as part of a measurement device with a measurement unit for measuring vital parameters of a fetus during labor and delivery. The sensor is attached to the presenting part of the fetus for the duration of labor and delivery. In order to prevent the arterial blood flow in the fetal tissue at the measurement point from being impaired by attachment of the sensor to the fetal tissue, the sensor has an approximately round, curved cup which forms a concavity on its concave side and is subdivided into an attachment zone at the center and an elastic peripheral zone surrounding it where the light emitter and receiver are arranged, whereby the peripheral zone of the cup attached to the fetal tissue rests in a flexible, spring-loaded manner on the fetal tissue.

26 Claims, 6 Drawing Sheets

SENSOR DEVICE FOR MEASURING VITAL PARAMETERS OF A FETUS DURING LABOR AND DELIVERY

FIELD OF THE INVENTION

This invention concerns a sensor device as part of a measurement device with a measurement unit for measuring vital parameters of a fetus during labor and delivery, especially the fetal blood oxygen level, whereby the sensor device has a carrier with an approximately round cross section and with a concavity in which at least one light emitter and at least one receiver are arranged, and approximately at the center of which is a device for attaching the carrier to the presenting part of the fetus.

BACKGROUND OF THE INVENTION

Such a sensor device has been disclosed by German Patent 3,810,008, FIG. 5.

In said patent, the carrier is designed in the form of a cylinder at one end of which there is a concavity with a considerable depth from which a spiral wire as the attachment device projects a relatively great distance. The carrier is made of a practically inflexible material. The light emitter and receiver are arranged opposite each other close to the edge of the concavity.

Fetal tissue is drawn into the concavity with the spiral so that light can be passed through the fetal tissue that is drawn into the concavity.

Within the context of this invention, it has been found that when tissue is drawn into the concavity, the arterial blood flow in this area can be impaired to the extent that no analyzable signals can be received.

With another known sensor device (European Patent 135,840, FIGS. 10 and 11), the carrier is designed as a hollow suction cup of silicone rubber with a vacuum hose leading into the concavity thereof from one side, while the opposite wall is equipped with slits arranged in a star pattern to allow the passage of air and also has a light emitter and a receiver. It is difficult to secure the suction cup reliably by means of a vacuum during the labor and delivery process, and the relatively stiff vacuum hose also causes problems.

It should be noted here that this cannot be accomplished with a weak vacuum in any case. However, if a much higher vacuum is applied, the arterial blood flow at the point of measurement in the fetal tissue is interrupted by the high pressure applied by the vacuum. Therefore, attaching the carrier by means of a vacuum of the type known previously is not very promising.

SUMMARY OF THE INVENTION

The object of the present invention is therefore to design a sensor device so as to assure that analyzable signals can be received for the duration of the labor and delivery process after attaching the sensor to the fetal tissue.

To achieve this object, the carrier of the sensor device of the present invention is designed as a curved cup which forms the concavity on its concave side and is subdivided into an attachment zone at the center and an elastic peripheral zone surrounding it, with the light emitter and receiver arranged in the peripheral zone, whereby the peripheral zone of the cup attached to the fetal tissue is in flexible, spring-loaded contact with the fetal tissue.

Due to the central holding force and the approximately round cup shape of the sensor, the peripheral zone is pressed against the fetal tissue with a practically uniform initial tension.

The sensor is subdivided by this invention into two zones, namely a central zone where the attachment device secures the sensor against the fetal tissue and a peripheral zone that rests on the fetal tissue with such a gentle tension that the arterial blood flow of the fetus is in no case impaired in this zone. The light emitter and receiver are then located in this problem-free peripheral zone.

There is practically no concavity in the shape of the sensor (the cup) attached to the fetal tissue, and the surface of the concavity is in close contact with the fetal tissue.

The light emitter sends light into the fetal tissue where it propagates in all directions and some of the light strikes the receiver.

According to this invention, the attachment material may be designed and arranged as a wire spiral such that it is embedded with a part shaped in any desired manner in the material of the cup and the other part which is designed as a spiral projects by the length of approximately one turn out of the surface of the concavity.

Thus, a secure and nevertheless gentle attachment of the cup to the fetal tissue can be achieved by rotating the carrier and thus also the spiral approximately 360°.

However, the attachment device may also include an adhesive.

For the penetration of light into the fetal tissue, it is advantageous if the light emitter and receiver are partially embedded in the material of the cup and their surface is approximately flush with the surface of the concavity.

In order for the modulation of the received light to achieve a maximum, the material of the cup according to this invention may be of a color that is impermeable for the wavelengths of light used in this process or a color that absorbs those wavelengths of light.

However, in this regard it is also possible for the light emitter and receiver to be shielded to the rear inside the cup and for the surface of the concavity to have a color that absorbs the wavelengths of light used in the process.

In order for as much light as possible to find its way through the fetal tissue in the area of the peripheral zone to the receiver, it is advantageous for the light emitter(s) and receiver(s) to be arranged so they are approximately opposite each other relative to the center of the cup but preferably at an angle not equal to 180°.

An especially favorable effect can be achieved by providing two light emitters and one receiver and arranging them so they are each located approximately at one vertex of a triangle. Then the attachment zone may be arranged within this triangle.

DESCRIPTION OF THE DRAWING

Additional features and advantages of this invention will be better understood from the following description in conjunction with the figures which illustrate practical embodiments of this invention, namely:

FIG. 6 shows a detail of area VI in FIG. 2 greatly enlarged).

DETAILED DESCRIPTION OF THE INVENTION

Figure 1:
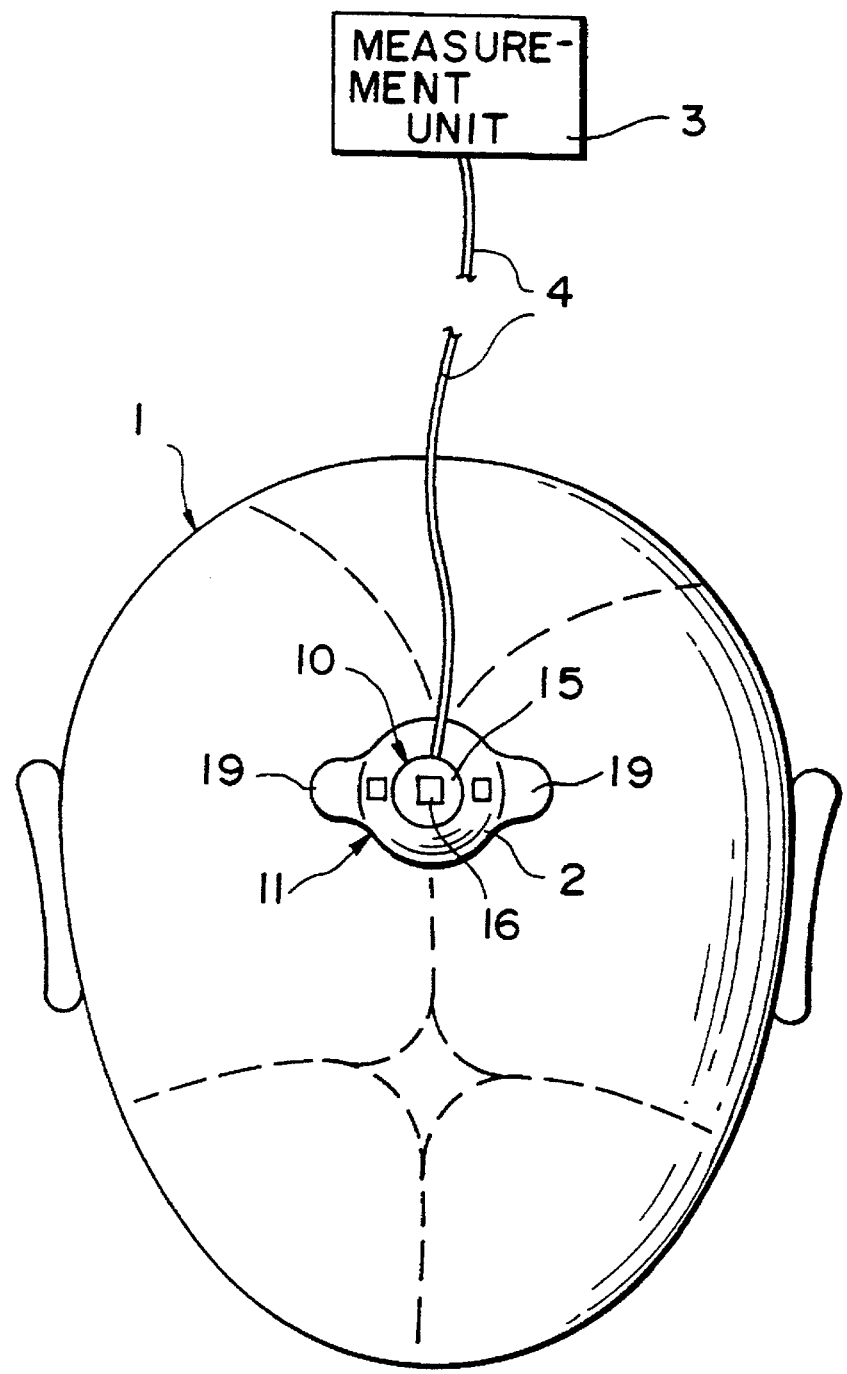
FIG. 1 shows a top view of the carrier (sensor) attached to the head of the fetus in combination with the measurement unit shown on an enlarged scale.

FIG. 1 shows the presenting part of the fetus in delivery, namely the head 1 in the example shown. The mother's birth canal has been omitted for reasons of simplicity.

The carrier 2 (sensor) is inserted through the vagina and attached to head 1.

Sensor 2 is connected to measurement unit 3 by lines (electric wires) labeled as 4 in general.

Figure 2:
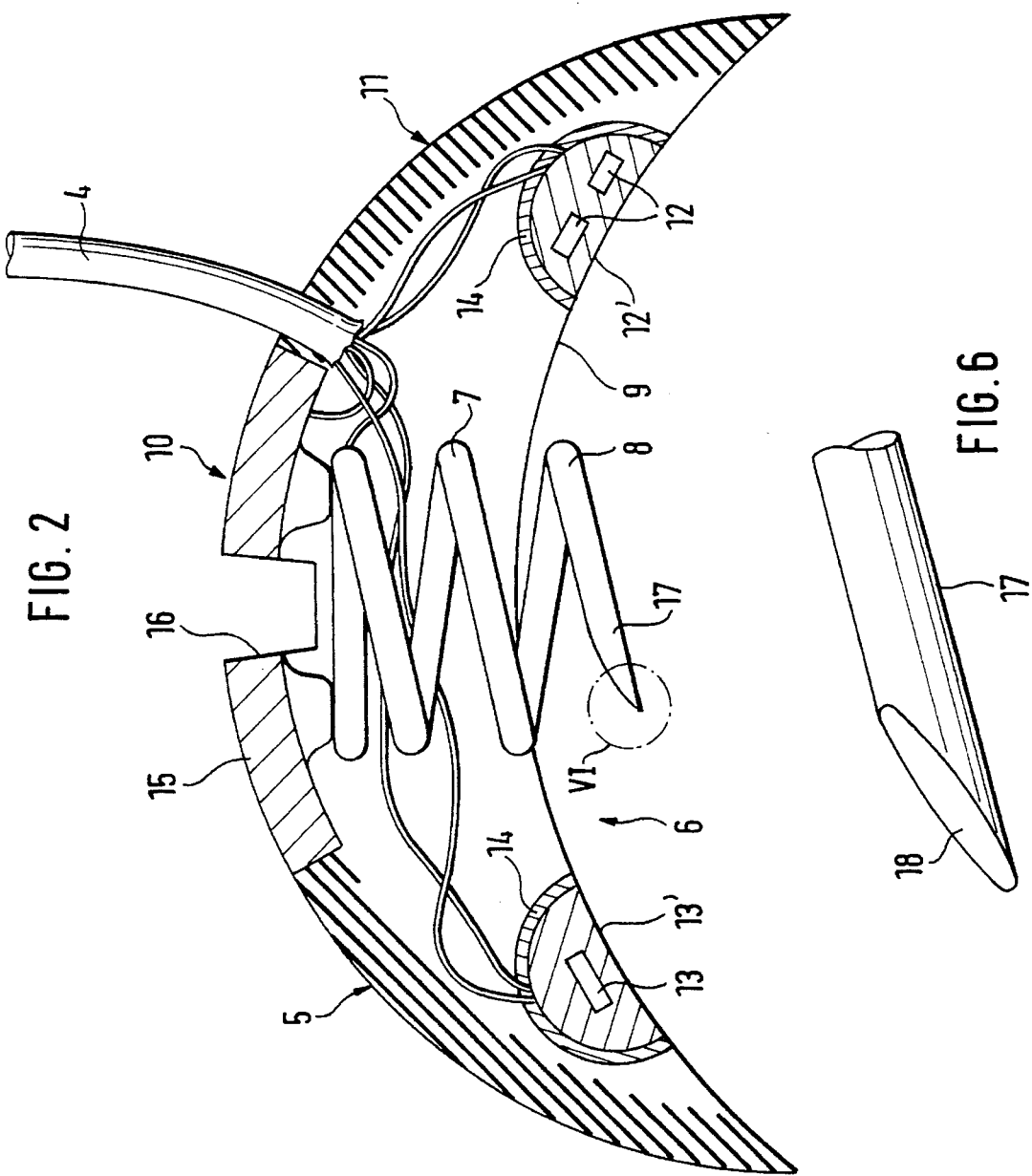
FIG. 2 shows an axial section through the undeformed carrier, greatly enlarged.

FIG. 2 shows the carrier 2 in a first embodiment where it is not attached to the head of the fetus, so therefore it is not deformed.

Carrier 2 is designed as a round cup 5 with a curved cross section that tapers significantly toward the edge. Cup 5 has a concavity 6 on the concave side facing the head 1 of the fetus.

Carrier 2 is made of a relatively soft rubbery material.

A spiral wire 7 is embedded in the center of cup 5 and projects by approximately the length of one turn 8 out of the surface 9 of concavity 6.

The carrier thus has a centrally arranged attachment zone 10.

This is surrounded by an elastic peripheral zone 11 where a light emitter 12 and a receiver 13 that are embedded in the material of peripheral zone 11 are arranged, whereby their surfaces 12' and 13' are approximately flush with the surface 9 of concavity 6. The curvature of the concavity 6 of cup 5 in the undeformed state is larger than the largest curvature of a fetal head according to statistics.

The light emitter 12 and the receiver 13 are each shielded optically at the rear by a cap 14 within cup 5. At the same time, the surface 9 of concavity 6 has a color that is impermeable for the wavelength of light used in the device or a color that absorbs that wavelength of light.

The same effects can be achieved if the material of cup 5 has a color that absorbs the wavelengths of light used in the process.

Figure 3:
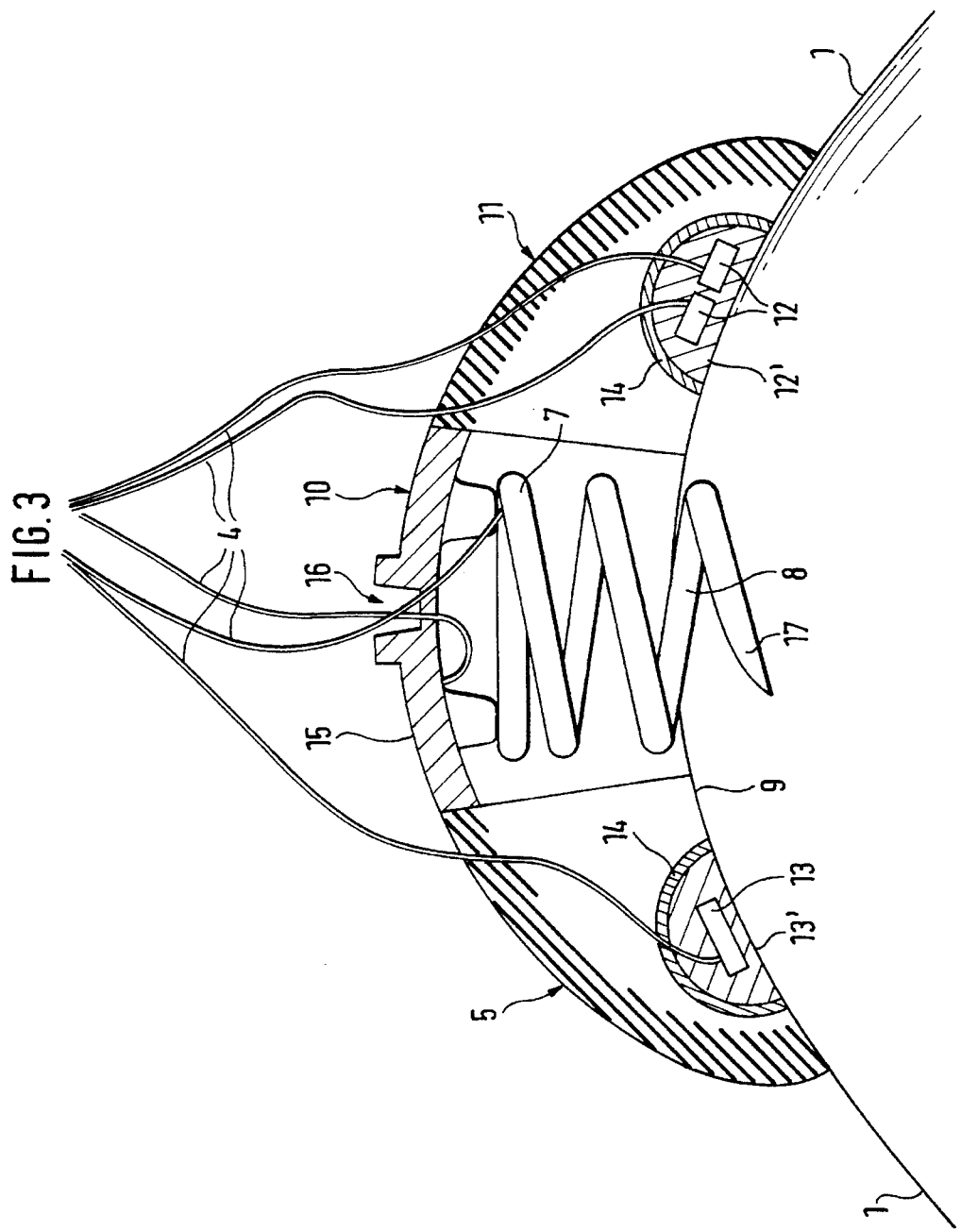
FIG. 3 shows an axial section through the carrier attached to the fetus—also greatly enlarged.

As shown in FIGS. 2 and 3, cup 5 is provided on its convex side with a metal plate 15 that is partially embedded in the material of cup 5 and is permanently connected there to spiral wire 7, but the metal plate and the spiral are electrically insulated with respect to each other.

Metal plate 15 forms a structural unit with an internal polygon 16 arranged in the center which serves as the coupling part for a rotating handle (not shown).

Lines 4 may pass through the coupling part—in other words, at the center of cup 5—in order to prevent lines 4 from exerting any torque on cup 5, whether when attaching it to the fetus or during delivery. The rotating handle may be designed as a fork on the proximal end, for example, in which case lines 4 are introduced into the side of the fork.

One separate line 4 leads to the metal plate 15 and another leads to the spiral wire 7, so these parts can serve directly as ECG electrodes.

The light emitter 12 and receiver 13 are each connected to measurement unit 3 by their own lines (electric wires) 4.

The end 17 of spiral wire 7 is shown in FIG. 6. The end 17 is provided with an inclined edge 18 pointing toward the head 1 of the fetus in order to form a small cutting edge.

Figure 4:
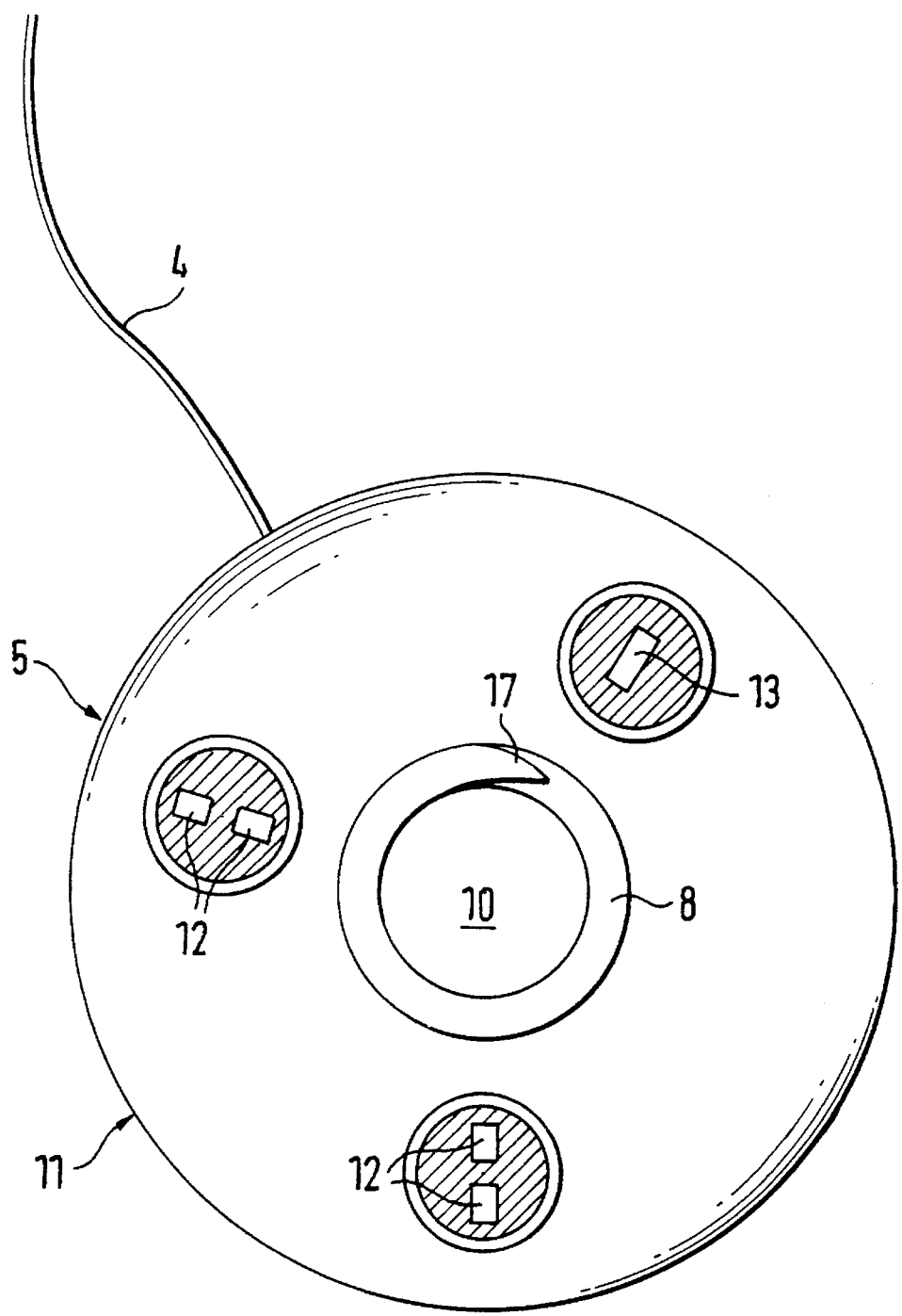
FIG. 4 shows a view of the bottom of the carrier (sensor) in a first embodiment—also greatly enlarged.

FIG. 4 shows an arrangement of two light emitters 12 and one receiver 13, each of which is arranged at the vertex of a triangle.

Figure 5:
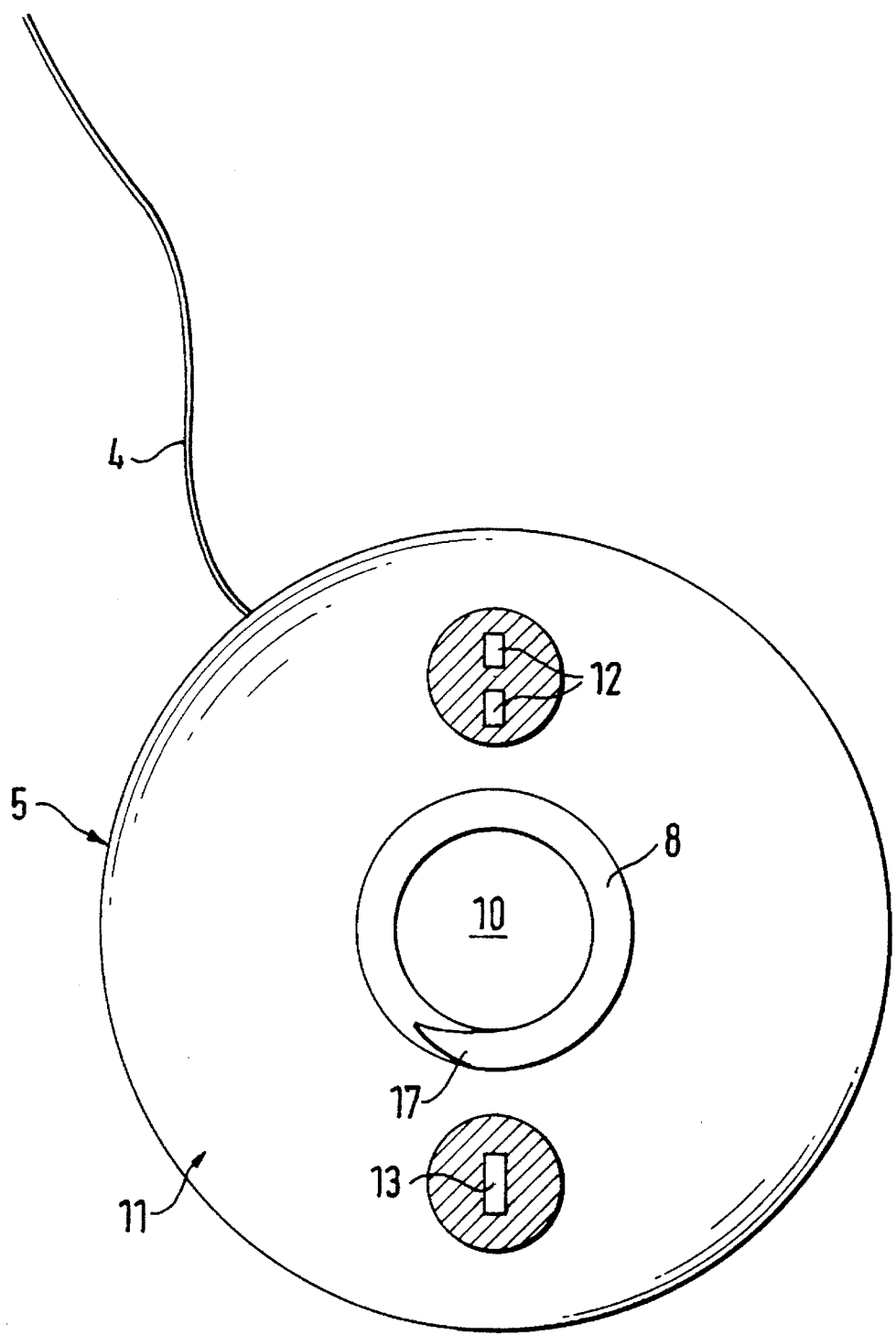
FIG. 5 shows a view of the bottom of the carrier (sensor) in a second embodiment, also greatly enlarged.

Each light emitter 12 and receiver 13 is thus approximately opposite the center of cup 5 but arranged at an angle not equal to 180°, as shown in FIG. 5, where there is one light emitter 12 and one receiver 13.

In a preferred embodiment, the diameter of cup 5 is approximately 14 mm and the thickness of the cup at the center is approximately 2 mm, while the Shore hardness is approximately 30 Shore.

The elasticity of peripheral zone 11 and its suppleness can be achieved to the required extent through the choice of the Shore hardness of the material and by varying the thickness of the cup and also by tapering it.

The function and operation of the sensor device is explained below.

The small dimensions of the carrier 2 and its ease of handling permit carrier 2 to be introduced through the vagina and attached to the presenting part of the fetus at a very early stage of labor.

To do so, the carrier 2 is pressed lightly at the center against the head of the fetus, for example, by a rotating handle having a polygonal profile on the distal end that fits into the polygonal profile 16 of cup 5.

Spiral wire 7 is twisted into the fetal tissue by a 360° rotation of carrier 2. Since spiral 7 projects only the distance of one turn out of the surface 9 of concavity 6, one complete rotation of carrier 2 assures that the proximal turn of spiral 7 has been twisted into the fetal tissue without causing any impairment in the fetal tissue. In this regard, the beveled edge 18 at the end of spiral 7 is also helpful in assuring that the sharpened end will penetrate immediately into the fetal tissue when spiral 7 presses on the fetal tissue and then is twisted.

The rotational force is transmitted directly by way of the polygonal profile and metal plate 15 to spiral 7 which is permanently connected to it.

When carrier 2 is pressed at the center against the fetal tissue, the peripheral zone 11 of cup 5 is the first to come in contact with the fetal tissue. The peripheral zone 11 then undergoes elastic deformation and the curvature of cup 5 is reduced. When spiral 7 has been twisted into the fetal tissue, the peripheral zone 11 of cup 5 rests with a slight initial tension on the fetal tissue, so the surfaces of light emitter 12 and receiver 13 are also in contact with the fetal tissue.

The attachment zone 10 is also pressed by spiral 7 against the fetal tissue. The pressing of carrier 2 against the fetal tissue thus takes place very gently but tightly at the center as well, but in any case this prevents any impairment of the fetal arterial blood flow in the area of peripheral zone 11.

The light is transmitted from emitter 12 into the fetal tissue where it propagates in all directions, so some of the light also strikes receiver 13. The best modulation is achieved when the light emitter and receiver are arranged as illustrated in FIG. 4 or 5. However, the light propagates in all directions in the fetal tissue (unlike in other media) so that enough light would still strike receiver 13 even if the emitter and receiver were arranged so they were diametrically opposed.

It is also important from the standpoint of light efficiency to prevent loss of light. In particular, light should be prevented from being short-circuited from the emitter to the receiver without passing through the fetal tissue.

This disadvantage can be avoided if the material of cup 5 has a color that is impermeable for the wavelengths of light used in the process or a color that absorbs those wavelengths of light.

The light then cannot enter the material of cup 5 nor can the short circuit effect occur if a small gap remains between the surface of the emitter or receiver and the fetal tissue.

The same effect can be achieved if the emitter and receiver are optically shielded at the rear by a cap 14 and if the surface 9 of concavity 6 is provided with a color that absorbs the wavelengths of light used in the process.

As shown in FIG. 1, a tab-shaped ear 19 that projects radially outward beyond cup 5 and covers the fetal tissue in this area to prevent light from entering or being emitted can be attached in the area of emitter(s) 12 and/or a receiver(s) 13. The light propagates radially beyond the area of the cup in an area of approximately 8 mm in the fetal tissue. Therefore, it is advantageous to cover this area with ears 19.

Figure 5A:
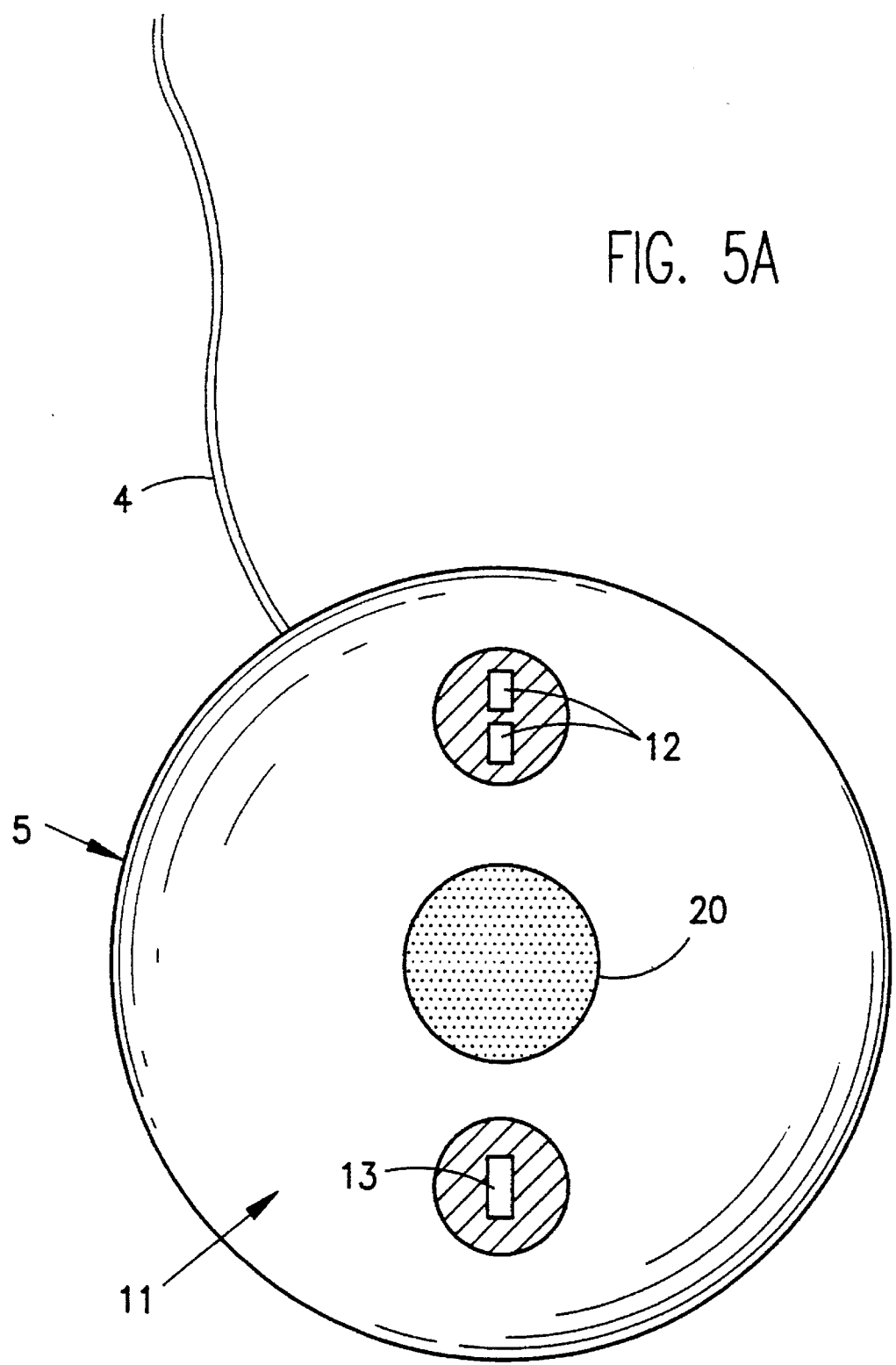
FIG. 5A shows a view of the bottom of the carrier (sensor) in the second embodiment, also greatly enlarged, with the use of an adhesive to attach the carrier to the fetus.

As shown in FIG. 5A, carrier 2 can also be attached to the fetal tissue in such a way than the center of cup 5 is attached to the fetal tissue by an adhesive layer 20.

Other methods of attachment may also be used as long as it is certain that the peripheral zone 11 of the cup can yield in an elastic, spring-loaded manner when the carrier is pressed against the fetal tissue and as long as the peripheral zone rests on the fetal tissue with a slight initial tension.

However, attaching the carrier 2 by the spiral wire 7 also offers the possibility that the parts which are electrically insulated with respect to each other, namely the metal plate 15 and the spiral 7, can be used as electrodes, for example, as ECG electrodes.

The especially simple design of the carrier 2 and its very small shape should be emphasized.

The carrier 2 can be produced very easily and economically (as a disposable item).

Nevertheless, carrier 2 fulfills in an excellent manner the object of a reliable and durable means of attachment to the fetal tissue and satisfactory reception of signals for the purpose of measuring vital parameters of a fetus during labor and delivery.

What is claimed is:

1. A sensor for measuring during labor and delivery the vital parameters of a fetus having a presenting part without impairing the arterial blood flow in the fetus at the point of measurement, said sensor comprising:
   a carrier defining a curved cup and having:
   (a) an approximately round cross section with a center,
   (b) a concave surface adapted to face the presenting part of the fetus and forming a concavity,
   (c) an attachment zone at said center of said carrier, and
   (d) an elastic peripheral zone surrounding said attachment zone and in flexible, spring-loaded contact with fetal tissue when said carrier is attached to the presenting part of the fetus;
   at least one light emitter arranged in said elastic peripheral zone;
   at least one light receiver arranged in said elastic peripheral zone; and
   means for attaching said carrier to the presenting part of the fetus so as to permit the flexible, spring-loaded contact of the peripheral zone, said attaching means located at said center of said carrier.

2. A sensor as claimed in claim 1 wherein said attaching means is a spiral wire having a first end embedded in said carrier and a second end formed as a spiral projecting about one turn out of said concave surface of said carrier.

3. A sensor as claimed in claim 2 wherein said carrier has a convex surface opposite said concave surface and means for coupling said carrier to a rotating handle, said coupling means located in the center of said convex surface of said carrier.

4. A sensor as claimed in claim 3 wherein said coupling means forms an internal polygon.

5. A sensor as claimed in claim 3 wherein said coupling means is a structural metal plate partially embedded in said carrier and permanently connected to said spiral wire.

6. A sensor as claimed in claim 5 wherein said structural metal plate and said spiral wire are electrically insulated from each other and are each connected to a separate electric line.

7. A sensor as claimed in claim 6 wherein said electric lines pass through said structural metal plate located in the center of said convex surface of said carrier.

8. A sensor as claimed in claim 6 wherein said electric lines pass through said structural metal plate located in the center of said convex surface of said carrier.

9. A sensor as claimed in claim 2 wherein said second end of said spiral wire has a sharpened surface pointing toward said carrier.

10. A sensor as claimed in claim 1 wherein said attaching means is an adhesive.

11. A sensor as claimed in claim 1 wherein said light emitter and said light receiver are partially embedded in said carrier, each having an exposed surface substantially flush with said concave surface of said carrier.

12. A sensor as claimed in claim 1 wherein said carrier is a color that is one of (a) impermeable for the wavelengths of light emitted by said light emitter and (b) absorbant for the wavelengths of light emitted by said light emitter.

13. A sensor as claimed in claim 1, wherein said light emitter and said light receiver each have a rear surface, said sensor further comprising a cap for each light emitter and light receiver, said caps embedded in said carrier and disposed around and shielding said rear surface of each of said light emitter and light receiver.

14. A sensor as claimed in claim 13 wherein said concave surface of said carrier is a color that absorbs the wavelengths of light emitted by said light emitter.

15. A sensor as claimed in claim 1 wherein said light emitter and said light receiver are approximately opposite each other relative to said center of said carrier.

16. A sensor as claimed in claim 1 further comprising two light emitters and one light receiver, said light emitters and said light receiver each arranged approximately at one vertex of a triangle.

17. A sensor as claimed in claim 1 wherein said carrier has a diameter of approximately 14 mm, a thickness of approximately 2 mm, and a hardness of approximately 30 Shore.

18. A sensor as claimed in claim 1 further comprising at least one tab-shaped ear attached to and projecting radially outward from said carrier adjacent one of said light emitter and said light receiver.

19. A sensor as claimed in claim 1 wherein said attaching means is a spiral wire having an end embedded in said carrier.

20. A sensor as claimed in claim 1, wherein the light emitter and the light receiver are arranged in non-diametrically opposed positions.

21. A sensor as claimed in claim 1, wherein the light emitter and the light receiver are arranged such that a major portion of a light path from the light emitter to the light receiver is outside of the attachment zone where blood flow is restricted.

22. A sensor for measuring during labor and delivery the vital parameters of a fetus having a presenting part without impairing the arterial blood flow in the fetus at the point of measurement, said sensor comprising:

a carrier defining a curved cup and having:
(a) an approximately round cross section with a center,
(b) a concave surface adapted to face the presenting part of the fetus and forming a concavity,
(c) a convex surface opposite said concave surface,
(d) an attachment zone at said center of said carrier, and
(e) an elastic peripheral zone surrounding said attachment zone and in flexible, spring-loaded contact with fetal tissue when said carrier is attached to the presenting part of the fetus;

at least one light emitter arranged in said elastic peripheral zone;

at least one light receiver arranged in said elastic peripheral zone;

a spiral wire having a first end embedded in said carrier at said center of said carrier and a second end formed as a spiral projecting about one turn out of said concave surface of said carrier for attaching said carrier to the presenting part of the fetus; and a structural metal plate partially embedded in said carrier and permanently connected to said spiral wire, located in the center of said convex surface of said carrier, for coupling said carrier to a rotating handle.

23. A sensor as claimed in claim 22 wherein said structural metal plate and said spiral wire are electrically insulated from each other and are each connected to a separate electric line.

24. A sensor for measuring during labor and delivery the vital parameters of a fetus having a presenting part without impairing the arterial blood flow in the fetus at the point of measurement, said sensor comprising:

a carrier defining a curved cup and having:
(a) an approximately round cross section with a center,
(b) a concave surface adapted to face the presenting part of the fetus and forming a concavity,
(c) an attachment zone at said center of said carrier, and
(d) an elastic peripheral zone surrounding said attachment zone and in flexible, spring-loaded contact with fetal tissue when said carrier is attached to the presenting part of the fetus;

at least one light emitter arranged in said elastic peripheral zone;

at least one light receiver arranged in said elastic peripheral zone; and means for attaching said attachment zone of said carrier to the presenting part of the fetus so as to permit the flexible, spring loaded contact of the peripheral zone, said attaching means located at said attachment zone at said center of said carrier.

25. A sensor as claimed in claim 24, wherein the light emitter and the light receiver are arranged in non-diametrically opposed positions.

26. A sensor as claimed in claim 24, wherein the light emitter and the light receiver are arranged such that a major portion of a light path from the light emitter to the light receiver is outside of the attachment zone where blood flow is restricted.

* * * * *